US012220863B2

(12) United States Patent
Beers Post et al.

(10) Patent No.: US 12,220,863 B2
(45) Date of Patent: Feb. 11, 2025

(54) MEDICAL DEVICES AND METHODS FOR FORMING MEDICAL DEVICES CONTAINING A BUILD PLATE

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Zachary John Beers Post, Memphis, TN (US); Vivek Pawar, Germantown, TN (US); Dawn Ryan McLean, Eads, TN (US); Roger Ryan Dees, Jr., Drummods, TN (US); Brad Dacus, Memphis, TN (US); Sean Haddock, Germantown, TN (US)

(73) Assignees: SMITH & NEPHEW, INC., Memphis, TN (US); SMITH & NEPHEW ORTHOPAEDICS AG SMITH, Zug (CH); NEPHEW ASIA PACIFIC PTE. LIMITED, Singapore (SG)

( * ) Notice: Subject to any disclaimer, the term of this patent is extended or adjusted under 35 U.S.C. 154(b) by 511 days.

(21) Appl. No.: 17/602,657

(22) PCT Filed: Apr. 8, 2020

(86) PCT No.: PCT/US2020/027261
§ 371 (c)(1),
(2) Date: Oct. 8, 2021

(87) PCT Pub. No.: WO2020/210353
PCT Pub. Date: Oct. 15, 2020

(65) Prior Publication Data
US 2022/0168106 A1  Jun. 2, 2022

Related U.S. Application Data

(60) Provisional application No. 62/832,683, filed on Apr. 11, 2019.

(51) Int. Cl.
*A61F 2/30* (2006.01)
*B22F 10/28* (2021.01)
(Continued)

(52) U.S. Cl.
CPC ........ *B29C 64/153* (2017.08); *A61F 2/30771* (2013.01); *A61F 2/3094* (2013.01);
(Continued)

(58) Field of Classification Search
None
See application file for complete search history.

(56) References Cited

U.S. PATENT DOCUMENTS 4,401,726 A * 8/1983 Gnanamuthu .......... C23C 26/02
219/121.66
4,542,539 A * 9/1985 Rowe, Jr. .................. A61F 2/30
606/76
(Continued)

FOREIGN PATENT DOCUMENTS

CN   101122019 A   2/2008
CN   201300207 Y   9/2009
(Continued)

OTHER PUBLICATIONS

International Search Report and Written Opinion for International application No. PCT/US2020/027261, mailed on Jun. 26, 2020, 15 pages.
(Continued)

*Primary Examiner* — Jeffrey A Vonch
(74) *Attorney, Agent, or Firm* — KDW Firm PLLC

(57) ABSTRACT

Medical devices, such as implants, and corresponding methods of manufacturing using an additive manufacturing technique, wherein the finished medical devices include a build plate retained therein, are disclosed. In some embodiments, the medical device includes a build plate having a plurality
(Continued)

of peaks and a plurality of indentations, the plurality of peaks and the plurality of indentations together defining a surface roughness of an exterior surface of the build plate. The medical device may further include a first layer formed atop the exterior surface of the build plate, the first layer comprising a plurality of powder structures disposed over the plurality of peaks and the plurality of indentations. In some embodiments, an average peak distance between adjacent peaks of the plurality of peaks is less than an average width dimension of at least a portion of the plurality of powder structures.

20 Claims, 7 Drawing Sheets

(51) Int. Cl.
| | |
|---|---|
| B29C 64/153 | (2017.01) |
| B29C 64/245 | (2017.01) |
| B32B 3/30 | (2006.01) |
| B32B 5/14 | (2006.01) |
| B33Y 10/00 | (2015.01) |
| B33Y 80/00 | (2015.01) |
| B29L 31/00 | (2006.01) |
| B32B 5/16 | (2006.01) |

(52) U.S. Cl.
CPC ............ *B29C 64/245* (2017.08); *B32B 3/30* (2013.01); *B32B 5/145* (2013.01); *B33Y 10/00* (2014.12); *B33Y 80/00* (2014.12); *A61F 2002/30321* (2013.01); *A61F 2002/30322* (2013.01); *A61F 2002/30962* (2013.01); *A61F 2002/30968* (2013.01); *A61F 2002/3097* (2013.01); *B22F 10/28* (2021.01); *B29L 2031/7532* (2013.01); *B32B 5/16* (2013.01); *B32B 2535/00* (2013.01); *Y10T 428/24479* (2015.01); *Y10T 428/24521* (2015.01); *Y10T 428/24529* (2015.01); *Y10T 428/24537* (2015.01); *Y10T 428/24579* (2015.01); *Y10T 428/24612* (2015.01); *Y10T 428/2462* (2015.01); *Y10T 428/24942* (2015.01)

(56) References Cited

U.S. PATENT DOCUMENTS

| | | | | |
|---|---|---|---|---|
| 5,549,697 A * | 8/1996 | Caldarise | ................. | A61F 2/34 623/22.14 |
| 5,768,134 A * | 6/1998 | Swaelens | ................. | B22F 5/00 700/121 |
| 5,876,550 A * | 3/1999 | Feygin | ................. | B29C 41/36 264/405 |
| 6,042,774 A * | 3/2000 | Wilkening | ............. | B33Y 70/00 264/460 |
| 6,491,985 B2 | 12/2002 | He | | |
| 7,497,876 B2 | 3/2009 | Tuke et al. | | |
| 8,524,142 B2 | 9/2013 | Uckelmann et al. | | |
| 9,949,837 B2 | 4/2018 | Wang et al. | | |
| 10,279,521 B1 * | 5/2019 | Pawar | .................... | B33Y 80/00 |
| 2002/0020164 A1* | 2/2002 | Cleveland | ................. | C23C 4/12 29/34 R |
| 2004/0191106 A1* | 9/2004 | O'Neill | ................... | B22F 10/80 419/2 |
| 2005/0184134 A1* | 8/2005 | Charlebois | .......... | A61F 2/30907 228/248.1 |
| 2007/0142914 A1* | 6/2007 | Jones | ................... | B23K 26/382 623/14.13 |
| 2008/0050412 A1* | 2/2008 | Jones | ................... | B33Y 80/00 427/2.24 |
| 2010/0137990 A1* | 6/2010 | Apatsidis | ............. | A61F 2/4425 606/301 |
| 2010/0204737 A1* | 8/2010 | Bae | ....................... | A61F 2/4455 606/279 |
| 2011/0241947 A1* | 10/2011 | Scott | ....................... | B22F 10/66 428/156 |
| 2012/0064290 A1* | 3/2012 | Esat | ....................... | A61L 27/34 428/161 |
| 2012/0253468 A1* | 10/2012 | Brooks | ............... | A61F 2/30767 427/2.26 |
| 2014/0086780 A1* | 3/2014 | Miller | ................. | A61F 2/30942 219/76.14 |
| 2014/0263196 A1* | 9/2014 | Daum | .................. | B23K 26/342 219/76.14 |
| 2014/0343687 A1* | 11/2014 | Jennissen | .................. | A61F 2/28 702/50 |
| 2014/0370323 A1* | 12/2014 | Ackelid | ................. | B23K 15/00 428/548 |
| 2015/0054193 A1* | 2/2015 | Meyer | ..................... | B22F 10/28 264/308 |
| 2015/0093283 A1* | 4/2015 | Miller | ................ | B23K 15/0086 264/109 |
| 2015/0335434 A1* | 11/2015 | Patterson | ............... | B23K 15/00 219/76.1 |
| 2016/0001401 A1* | 1/2016 | Dimter | ................. | B23K 26/342 219/76.12 |
| 2016/0144434 A1* | 5/2016 | Burd | ........................ | B22F 7/08 425/78 |
| 2017/0036400 A1* | 2/2017 | Loeffler | ............... | B29C 64/245 |
| 2017/0100210 A1* | 4/2017 | Wen | ...................... | A61C 7/08 |
| 2017/0291260 A1* | 10/2017 | McCarren | ............ | B29C 64/241 |
| 2017/0320270 A1* | 11/2017 | Mandel | .................. | B33Y 50/02 |
| 2018/0117854 A1* | 5/2018 | Hart | ...................... | B29C 64/20 |
| 2018/0214953 A1* | 8/2018 | Knittel | ..................... | B22F 3/22 |
| 2018/0264715 A1* | 9/2018 | Yoo | ......................... | B33Y 10/00 |
| 2018/0333782 A1* | 11/2018 | Gallagher | ............... | B22F 10/28 |
| 2018/0353642 A1* | 12/2018 | Lee | ........................... | A61F 2/34 |
| 2019/0134749 A1* | 5/2019 | Ott | ........................ | B23K 26/342 |
| 2020/0101534 A1* | 4/2020 | Gibson | .................. | B33Y 10/00 |
| 2020/0147866 A1* | 5/2020 | Van Egmond | ........ | B29C 64/232 |
| 2021/0022870 A1* | 1/2021 | Dewey | .................. | A61F 2/4455 |
| 2021/0114298 A1* | 4/2021 | Rodriguez Santiago | | ..................... A61F 2/3094 |

FOREIGN PATENT DOCUMENTS

| | | | | |
|---|---|---|---|---|
| CN | 103920877 A | * | 7/2014 | |
| CN | 108500455 A | * | 9/2018 | |
| CN | 110548871 A | * | 12/2019 | |
| DE | 19610015 A1 | | 9/1997 | |
| DE | 29808852 U1 | * | 9/1999 | ............ B22F 3/1055 |
| DE | 102008012063 A1 | * | 9/2009 | ............ B23K 26/34 |
| DE | 102008012064 A1 | * | 9/2009 | ............ B22F 3/1055 |
| DE | 102013221385 A1 | * | 4/2015 | ............ B22F 3/1055 |
| DE | 102015116409 A1 | * | 3/2017 | ............ A61F 2/3094 |
| DE | 102018203233 A1 | * | 9/2019 | |
| EP | 1803513 A2 | * | 7/2007 | ......... A61F 2/30942 |
| GB | 2458745 A | * | 10/2009 | ............. B22F 3/003 |
| KR | 2016078583 A | * | 7/2016 | |
| WO | WO-9611117 A1 | * | 4/1996 | ............... B22C 9/00 |
| WO | WO-0128733 A1 | * | 4/2001 | ............ B22F 3/1055 |
| WO | 2011048138 A1 | | 4/2011 | |
| WO | WO-2017087944 A1 | * | 5/2017 | ......... A61F 2/30771 |
| WO | WO-2017221912 A1 | * | 12/2017 | .............. B22F 3/105 |

OTHER PUBLICATIONS

Yuan, L., et al., "Additive manufacturing technology for porous metal implant applications and triple minimal surface structures: A review", Bioactive Materials 4:56-70 (2018).

\* cited by examiner

MEDICAL DEVICES AND METHODS FOR FORMING MEDICAL DEVICES CONTAINING A BUILD PLATE

CROSS-REFERENCE TO RELATED APPLICATION

This application is a National Phase filing of International Application No. PCT/US2020/027261, filed Apr. 8, 2020, which is a non-provisional of, and claims the benefit of U.S. Provisional Patent Application No. 62/832,683, filed Apr. 11, 2019, entitled "Medical Devices and Methods for Forming Medical Devices Containing a Build Plate," the entire contents of each application is hereby incorporated by reference in its entirety.

TECHNICAL FIELD

The present disclosure generally relates to medical devices, and more particularly, but not exclusively, to methods and medical devices, such as implants, formed using an additive manufacturing technique, the medical devices including a build plate retained therein.

BACKGROUND

Certain medical devices, such as orthopedic implants, can be formed using Solid Freeform Fabrication (SFF) or Rapid Prototyping (RP), for example, by additive manufacturing processes. Additive manufacturing techniques may include, for example, selective laser sintering (SLS), direct metal laser sintering (DMLS), electron beam melting (EBM), and selective laser melting (SLM) for the design, selection, development, manufacturing and/or finishing of medical devices.

In general, additive manufacturing techniques allow for structures to be built from three-dimensional models, including tessellated/triangulated solids and smooth solids. For example, in one embodiment, additive manufacturing techniques produce three-dimensional structures one layer at a time from a powder. In use, the initial layer may be placed onto a build plate. Thereafter, the powder may be solidified by irradiating a layer of the powder with an energy source such as a laser or an electron beam. The powder is fused, melted or sintered by the application of the energy source, which can be directed in raster-scan fashion to selected portions of the powder layer. After fusing a pattern in one powder layer, an additional layer of powder is dispensed, and the process is repeated with fusion taking place between the layers until the desired structure is complete. After the structure is complete, the structure is separated from the build plate(s).

For a number of reasons, it would be beneficial to utilize methods and medical devices, such as implants, formed via additive manufacturing, with a build plate in the final structure. As such, a need remains for further improvements in this technological field. The present disclosure addresses this need.

SUMMARY

The Summary is provided to introduce a selection of concepts in a simplified form, the concepts further described below in the Detailed Description. The Summary is not intended to identify key features or essential features of the claimed subject matter, nor is the Summary intended as an aid in determining the scope of the claimed subject matter.

Approaches for forming medical devices, such as medical implants, formed via additive manufacturing with a manufactured build plate interface included therein, are disclosed. In one embodiment, a medical device may include a build plate having a plurality of peaks and a plurality of indentations, the plurality of peaks and the plurality of indentations together defining a surface roughness of an exterior surface of the build plate. The medical device may further include a first layer formed atop the exterior surface of the build plate, the first layer comprising a plurality of powder structures disposed within the indentations and over the plurality of peaks, wherein an average peak distance between adjacent peaks of the plurality of peaks is less than an average width dimension of at least a portion of the plurality of powder structures.

In another embodiment, a method of forming a medical device may include providing a build plate, the build plate having a plurality of peaks and a plurality of indentations, the plurality of peaks and the plurality of indentations together defining a surface roughness of an exterior surface of the build plate. The method may further include forming a first layer atop the exterior surface of the build plate by depositing a plurality of powder structures over the plurality of peaks and within the plurality of indentations, at least a portion of the plurality of powder structures having an average width dimension that is greater than an average peak distance between adjacent peaks of the plurality of peaks. The plurality of powdered structures may then be thermally treated, wherein the first layer covers the plurality of peaks.

In another embodiment, a method of forming an implant may include providing a build plate, the build plate having a plurality of alternating peaks and indentations, the plurality of alternating peaks and indentations together defining a surface roughness of an exterior surface of the build plate. The method may further include forming a first layer atop the exterior surface of the build plate by depositing a plurality of powder structures over the plurality of alternating peaks and indentations, at least a portion of the plurality of powder structures having an average width dimension that is greater than an average peak distance between adjacent peaks of the plurality of alternating peaks and indentations. The method includes then heating the plurality of powder structures, wherein the first layer entirely covers the plurality of alternating peaks and indentations.

In these and other embodiments, the roughness of the surface of the build plate can be tailored to match one or more aspects of the morphology of the powder to be melted/sintered onto the build plate in order to improve adhesion at the interface thereof. For example, a mean peak width of the plurality of peaks may be tailored to be smaller than the mean powder size diameter, and/or another metric of the powder size, thus allowing the powder to flow smoothly over the indentations between the plurality of peaks. Additionally, the layer thickness of the deposited powder may be such that once laser-melted, the original surface profile of the build plate is entirely covered by the now-solid melted powder layer. In other words, the melted layer thickness will be greater than the peak height of the plurality of peaks of the surface of the build plate. One or more additional layer may then be laid upon the solid layer, and the additive process may continue.

Embodiments of the present disclosure provide numerous advantages. For example, the embodiments provide, inter alia, improved adhesion of the additively manufactured structure to the build plate.

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

The accompanying drawings illustrate exemplary approaches of the disclosure, including the practical application of the principles thereof, as follows.

Figure 1:
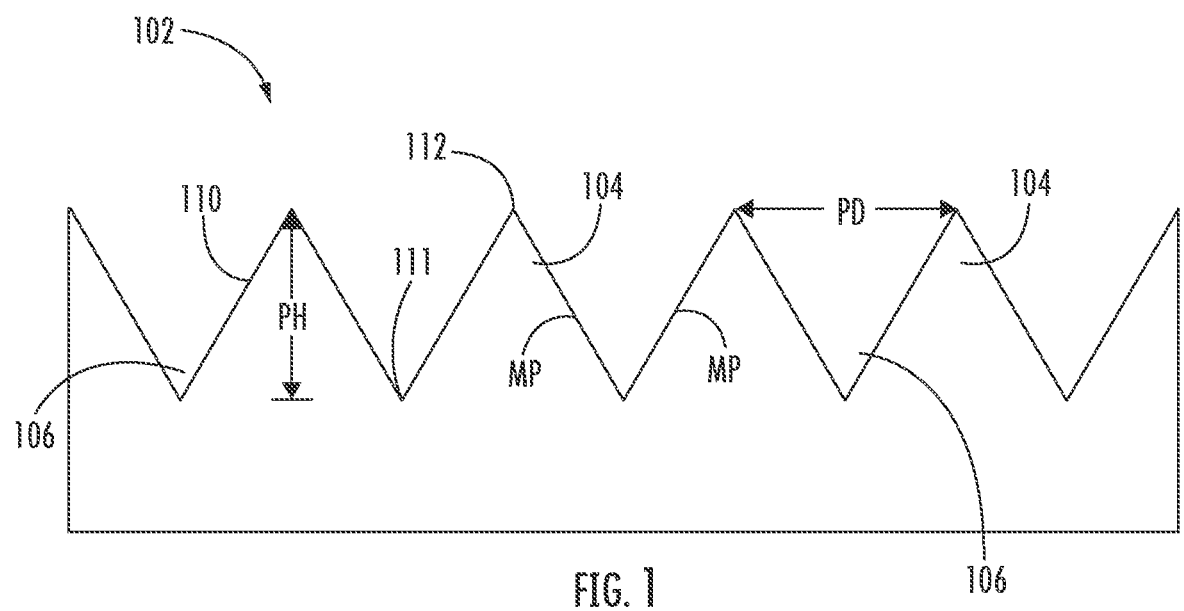
FIG. 1 illustrates a side, cross-sectional view of a surface of a build plate, in accordance with one aspect of the present disclosure.

The drawings are not necessarily to scale. The drawings are merely representations, not intended to portray specific parameters of the disclosure. The drawings are intended to depict example embodiments of the disclosure, and therefore are not be considered as limiting in scope. In the drawings, like numbering represents like elements.

Furthermore, certain elements in some of the figures may be omitted, or illustrated not-to-scale, for illustrative clarity. The cross-sectional views may be in the form of "slices", or "near-sighted" cross-sectional views, omitting certain background lines otherwise visible in a "true" cross-sectional view, for illustrative clarity. Furthermore, for clarity, some reference numbers may be omitted in certain drawings.

DESCRIPTION

For the purposes of promoting an understanding of the principles of the present disclosure, reference will now be made to example embodiments. It will nevertheless be understood that no limitation of the scope of the disclosure is thereby intended. Any alterations and further modifications in the described embodiments, and any further applications of the principles of the present disclosure as described herein are contemplated as would normally occur to one skilled in the art to which the disclosure relates.

The present disclosure is directed to medical devices, such as an implant, formed using an additive manufacturing technique and corresponding methods of manufacturing, wherein the medical devices (e.g., implants) include a build plate as part of the finished structure that is subsequently used to treat a patient. As noted above, generally speaking, currently known additive manufacturing techniques build an additively manufactured structure by placing a melted/sintered layer or layers of powder on a build plate. Thereafter, the build plate is removed from the melted/sintered layer(s) of powder prior to implantation of the implant. Thus arranged, the attachment strength of the additively manufactured structure to the build plate is often inadequate for an implantable implant. In order to address at least this deficiency of the prior art, embodiments of the present disclosure aim to improve the attachment strength between the melted/sintered layer or layers of powder structure and the build plate by optimizing various parameters, such as the surface roughness profile of the build plate, the size distribution of the powder, the shape of the powder, the power of the laser, the scan speed of the laser, and/or the layer thickness of the powder.

As described herein, embodiments of the present disclosure may be optimized to match the surface roughness of the build plate to one or more aspects of the morphology of the powder to be melted/sintered onto the plate in order to improve adhesion of the additively manufactured structure to the build plate. In some embodiments, a mean peak width of the plate surface profile may be tailored to be smaller than the mean powder size diameter, or another metric of the powder size. Additionally, the layer thickness of the deposited powder may be tailored so that once laser-melted, the original surface profile of the build plate will be entirely covered by the now-solid melted powder layer. Said differently, the melted layer thickness may be greater than a maximum peak height of the peaks of the surface of the build plate.

Referring to FIG. 1, a portion of a build plate 102 for building a medical device or a medical implant according to one example embodiment will be described. As shown, the build plate 102 may be a solid structure having a plurality of peaks 104 and a plurality of grooves, valleys, or indentations 106 formed therein. The build plate 102 may be formed by any variety of processes, such as additive manufacturing. Furthermore, the build 102 plate may be made from virtually any type of desired material such as, for example, titanium, commercially pure titanium, titanium alloy, cobalt-chromium, stainless steel, Zirconium, etc. The peaks 104 and the indentations 106 may be formed in the build plate 102 via machining, blasting, laser ablation, chemical etching, etc. Embodiments herein are not limited in this context. Together, the alternating peaks 104 and indentations 106 define a surface roughness of an exterior surface 110 of the build plate 102. In various embodiments, the peaks 104 and the indentations 106 may be sharp grooves, curved grooves, undercut features, etc. Although the peaks 104 are shown as being generally triangular-shaped, it will be appreciated that the peaks 104 may take on different shapes in other embodiments.

As shown, the peaks 104 may define a vertical peak height 'PH' measured from a bottom most point 111 of the indentations 106 to a tip 112 of peaks 104. Furthermore, the peaks 104 may define a peak distance 'PD' between adjacent peaks 104. In some embodiments, the peak distance may be measured between each tip 112 of adjacent peaks 104. In other embodiments, the peak distance may be measured at a midpoint 'MP' of each peak 104, the midpoint being a location approximately halfway between the bottom most point 111 and the tip 112. In some embodiments, the peak height and peak distance is substantially uniform across the build plate 102 for each of the peaks 104 and indentations 106. In other embodiments, the peak heights and peak distances can vary. Embodiments herein are not limited in this context.

Figure 2:
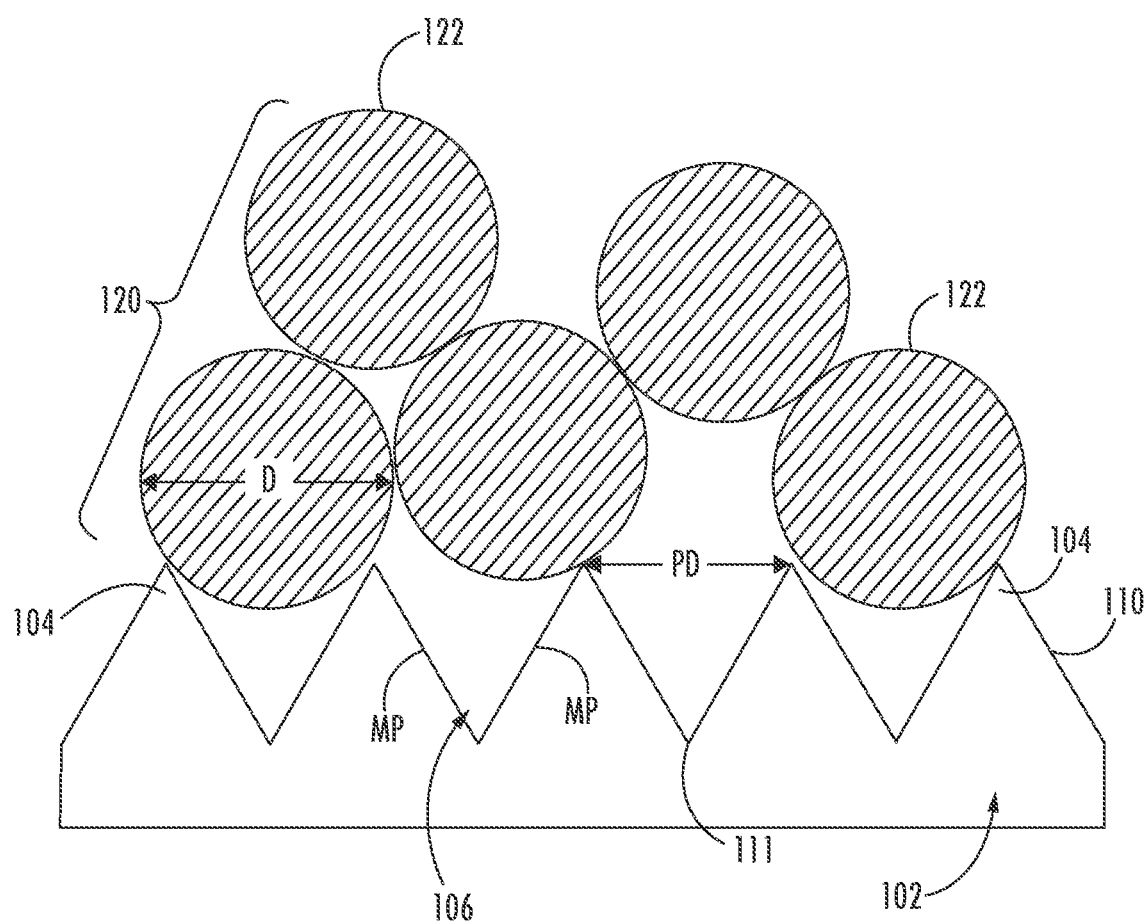
FIG. 2 illustrates a side, cross-sectional view of a surface of an example build plate with a plurality of powder structures formed thereon, in accordance with one aspect of the present disclosure.

In FIG. 2, a first layer 120 may be formed over, built on, or the like, the build plate 102. As shown, the first layer 120 may include a plurality of powder structures 122 disposed partially within the indentations 106 and over the peaks 104. Although non-limiting, the powder structures 122 may be a spherically shaped powders made from one or more polymers, one or more metals, sand, or other material(s). In some embodiments, the powder structures 122 and the build plate 102 may be the same or different materials. For example, the powder structures 122 may be a titanium alloy and the build plate 102 may be a zirconium alloy or a cobalt alloy. The powder structures 122 may each have a width dimension, such as a diameter 'D'. In some embodiments, the diameter of at least a portion of the powder structures 122 is greater than the peak distance 'PD' between adjacent peaks 104. In some embodiments, the powder diameter 'D' may be selected to ensure that the powder structures 122 are present above the midpoint 'MP' of the peaks 104, which enables better adhesion of the first layer 120 to the exterior surface 110 of the build plate 102 when the first layer 120 is thermally treated. For example, an average of the peak distances between adjacent peaks 104 may be less than an average of the width dimensions of the plurality of powder structures 122.

Figure 3:
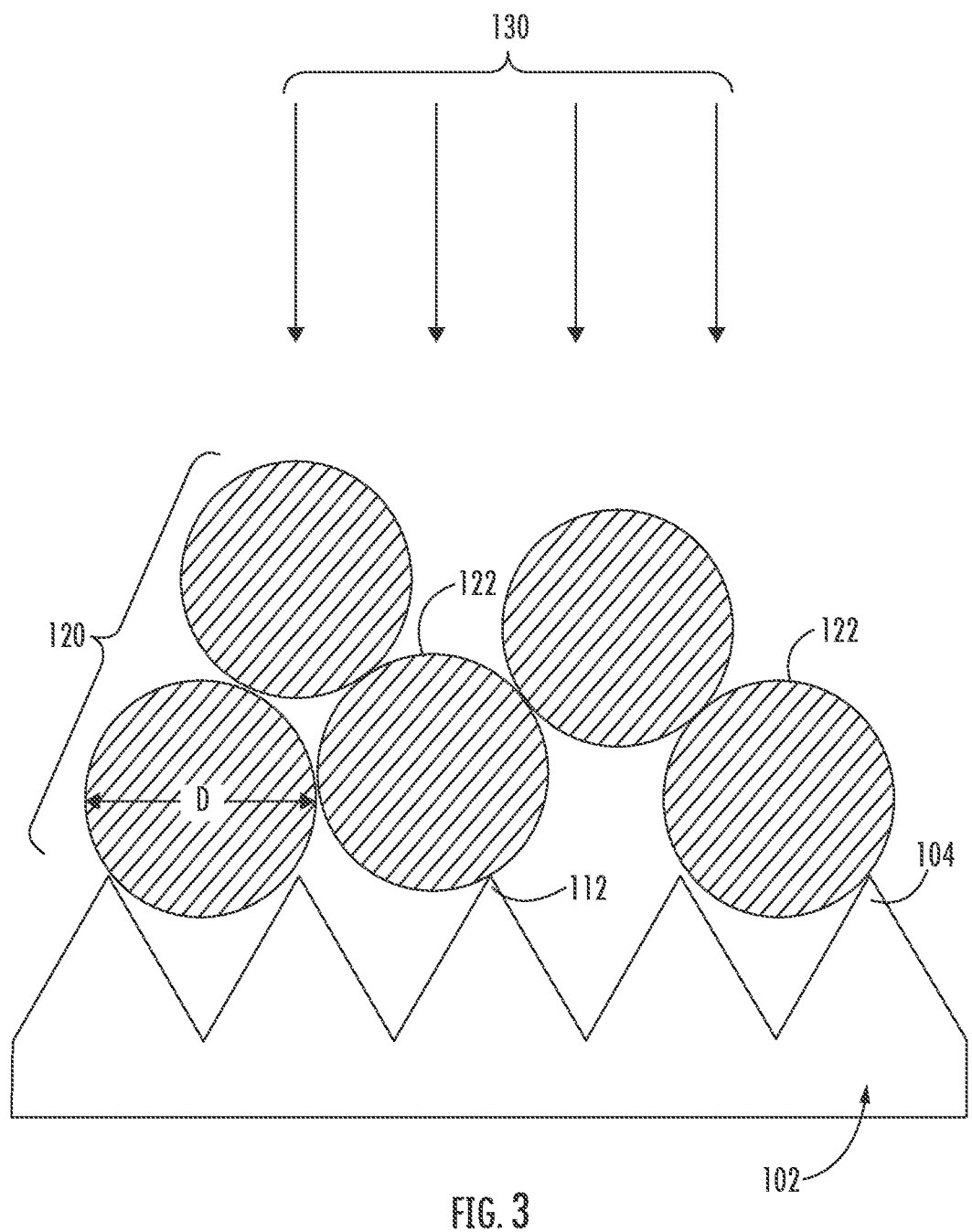
FIG. 3 illustrates a side, cross-sectional view of a thermal treatment to the example build plate and plurality of powdered structures of FIG. 2, in accordance with one aspect of the present disclosure.
Figure 4:
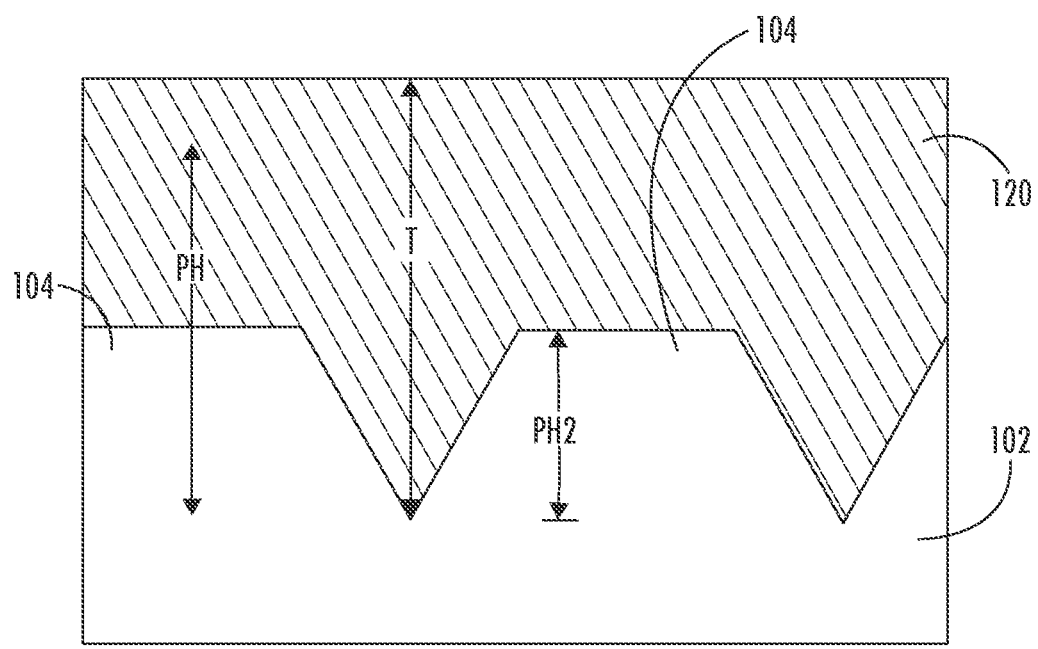
FIG. 4 illustrates a side, cross-sectional view of a first layer formed over the example build plate following the thermal treatment of FIG. 3, in accordance with one aspect of the present disclosure.

As shown in FIG. 3, the first layer 120 and the build plate 102 may receive a thermal treatment 130, for example, a laser or electron beam. Although embodiments herein are not limited to any particular process, the thermal treatment 130 may be a SLM manufacturing process, whereby a high-power laser scans the surface of the powder structures 122, generating heat that causes the powder structures 122 to melt and form a melt pool which solidifies as a consolidated first layer 120, as shown in FIG. 4. The first layer 120 may have a thickness 'T', which is greater than the original vertical peak height 'PH' of the peaks 104. Once formed, the first layer 120 covers each of the plurality of peaks 104. Furthermore, in some embodiments, at least some of the tips 112 (FIG. 3) of the peaks 104 melt during the thermal treatment 130, mixing together with the melted powder before solidifying into the first layer 120, as shown in FIG. 4. This melting and mixing together of the build plate 102 and the powder structures 122 increases adhesion of the first layer 120 and the build plate 102 at an interface thereof. As shown, the thermal treatment 130 may reduce a height of one or more of the peaks from the original vertical peak height to a second vertical peak height 'PH2'. In some embodiments, the laser power of the thermal treatment 130 may be adjusted to increase or decrease the second vertical peak height.

Figure 5:
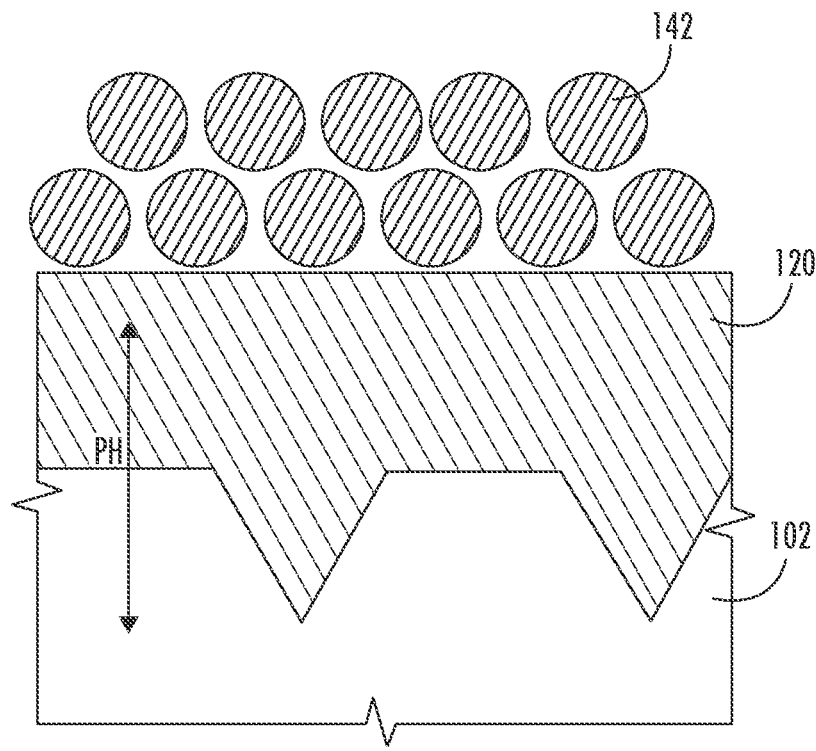
FIG. 5 illustrates a side, cross-sectional view of a surface of an example build plate with a second plurality of powder structures formed thereon, in accordance with one aspect of the present disclosure.
Figure 6:
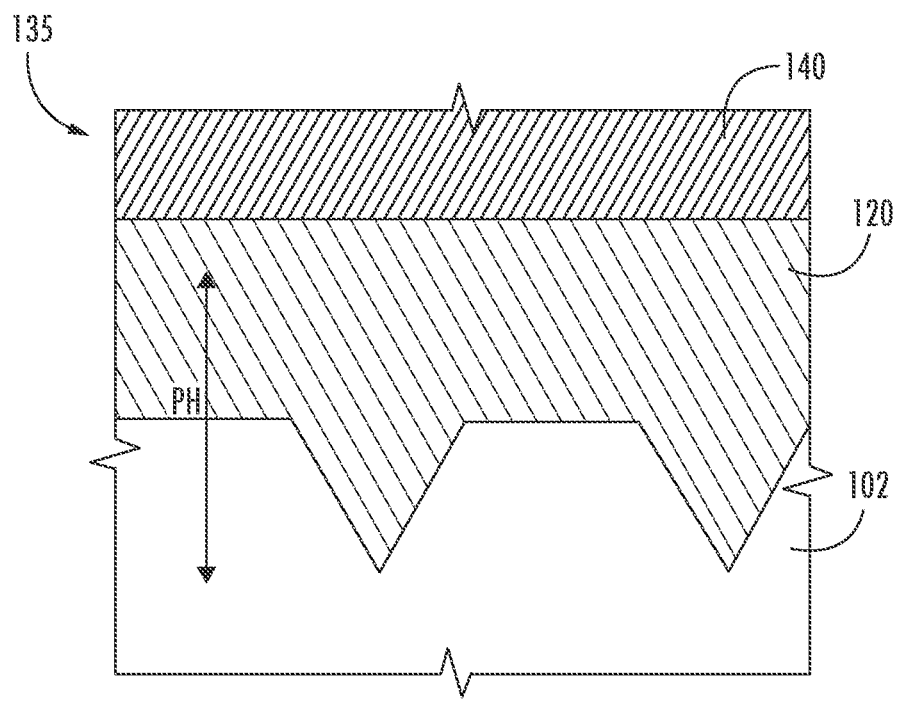
FIG. 6 illustrates a side, cross-sectional view of a second layer formed over the example build plate following a thermal treatment to the example build plate and the second plurality of powder structures of FIG. 5, in accordance with one aspect of the present disclosure.

In some embodiments, once the powder structures 122 have been scanned and relevant portions melted/solidified, a second plurality of powder structures 142 may be deposited atop the first layer 120, as shown in FIG. 5. The second plurality of powder structures 142 may similarly be melted using a thermal treatment to form a second layer 140 of the finished medical device 135, as shown in FIG. 6. The first and second layers 120, 140 may be the same or different materials. Although not shown, one or more additional layers may be similarly formed atop the second layer 140 using, for example, similar or different additive manufacturing techniques. Once layering is complete, the first layer 120, the optional second layer 140, etc., and the build plate 102, will be part of the finished medical device 135. That is, the build plate 102 forms part of the medical device 135 that is, for example, implanted into the patient.

As used herein, the medical device 135 may be any suitable implant or medical device now known or hereafter developed. For example, in some embodiments, the medical device 135 may be bone plate, a hip implant, a knee implant, etc. Embodiments of the present disclosure are not limited in this context.

Figure 7:
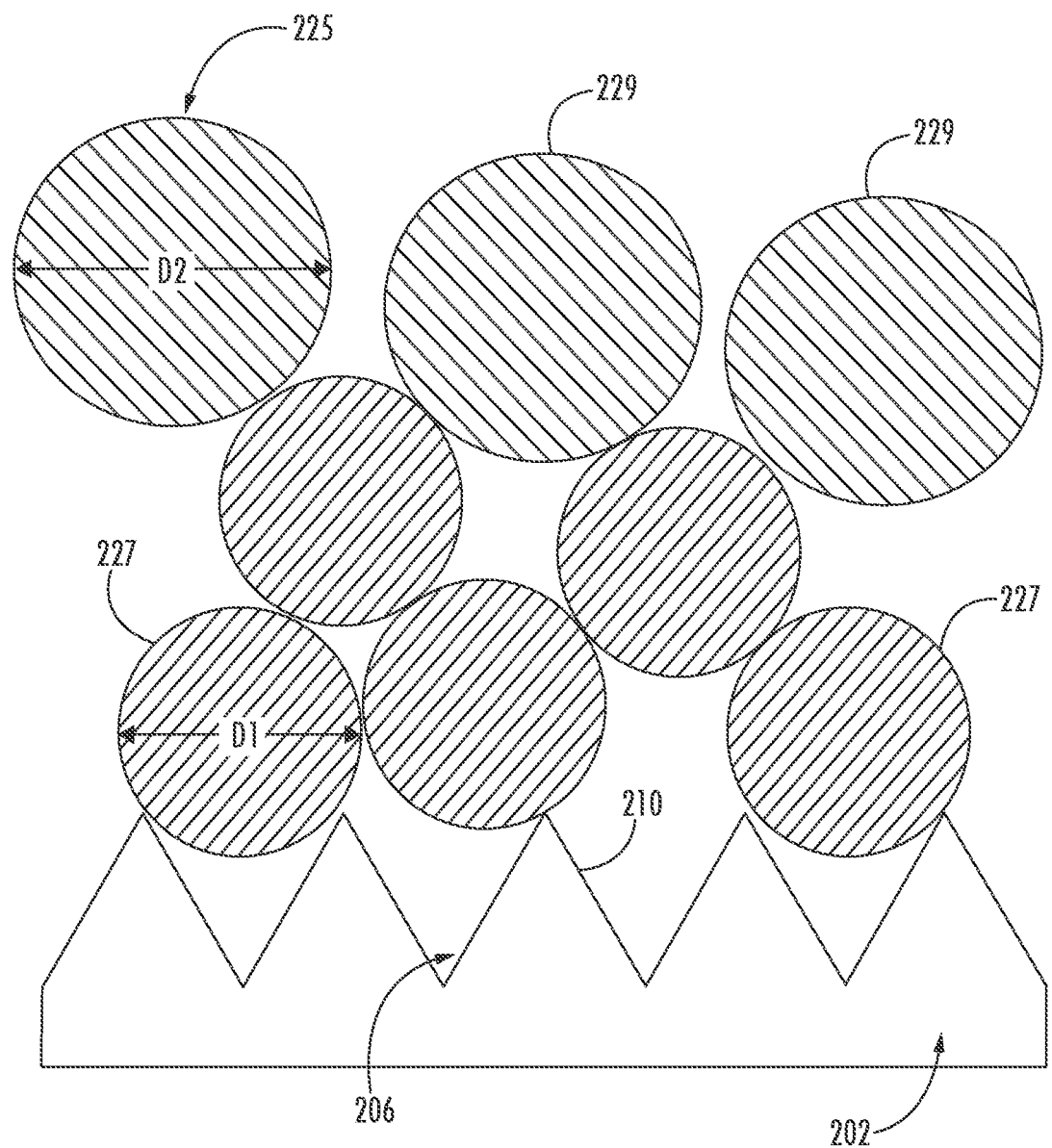
FIG. 7 illustrates a side, cross-sectional view of a surface of an example build plate with a plurality of powder structures formed thereon, in accordance with one aspect of the present disclosure.

Referring now to FIG. 7, an approach for forming a medical device according to embodiments of the present disclosure will be described. As shown, a plurality of powder structures 225 is provided atop an exterior surface 210 of a build plate 202. The build plate 202 may be the same or similar to the build plate 102 described above. As such, only certain aspects of the build plate 202 will hereinafter be described for the sake of brevity. As shown, the plurality of powder structures 225 may include a first group 227 and a second group 229, wherein the first group 227 may be disposed directly atop the build plate 202. Although non-limiting, the plurality of powder structures 225 may be spherically shaped powders made from one or more polymers, one or more metals, sand, or other material(s).

The first group 227 may have a first group average diameter 'D1', while the second group 229 may have a second group average diameter 'D2.' In this embodiment, D2 may be greater than D1. In other embodiments, D1 may be greater than D2. In some embodiments, the first group 227 is deposited on the build plate 202 before the second group 229. In other embodiments, the first and second groups 227, 229 may be deposited simultaneously. Embodiments herein are not limited in this context. After the first and second groups 227, 229 are deposited, the plurality of powder structures 225 may receive a thermal treatment, such as high-power laser scan, as described above.

Figure 8:
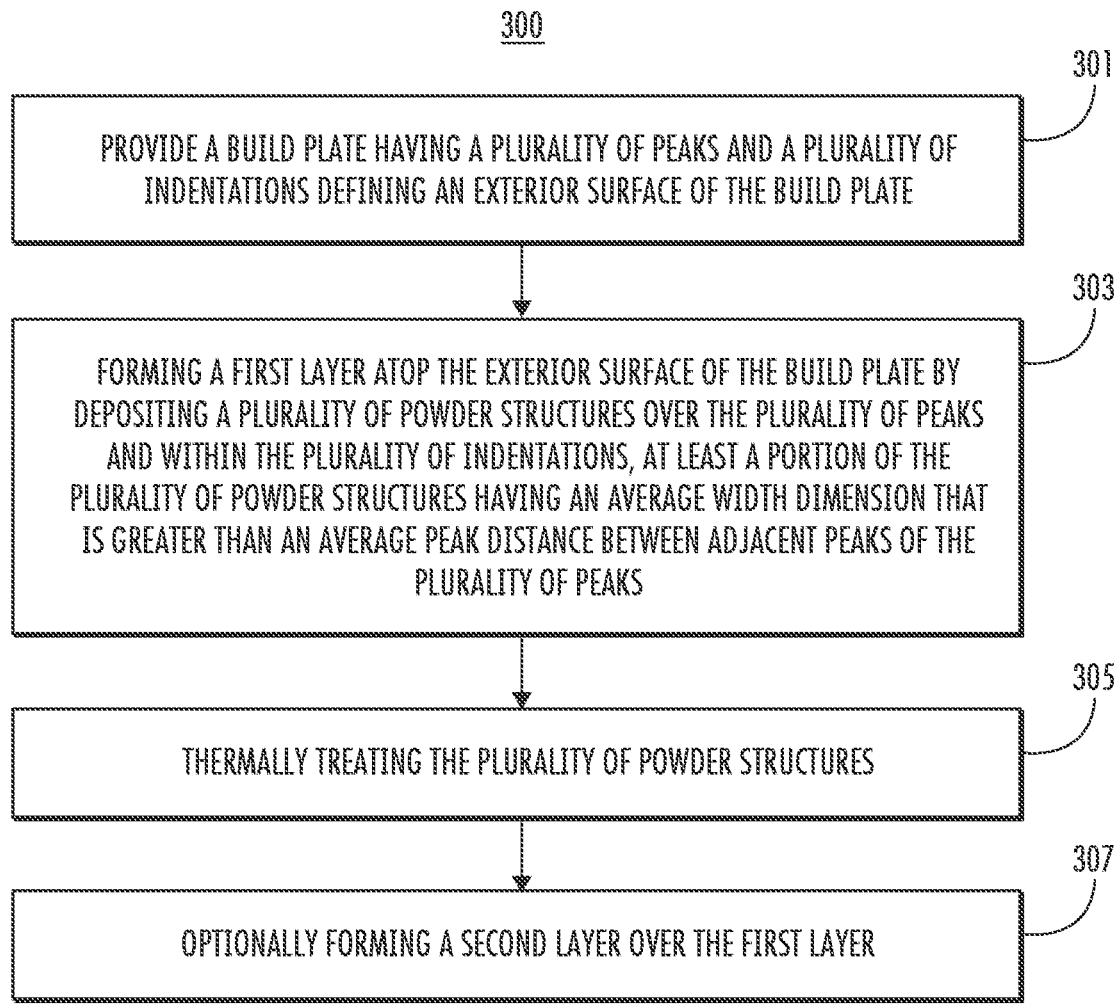
FIG. 8 is a flowchart illustrating a method for forming a medical device in accordance with one aspect of the present disclosure.

Referring to FIG. 8, an example of a method 300 for forming a medical device, such as an implant, will be described in greater detail. At block 301, the method 300 may include providing a build plate, the build plate having a plurality of peaks and a plurality of indentations, the plurality of peaks and the plurality of indentations together defining a surface roughness of an exterior surface of the build plate. In some embodiments, the peaks and the indentations of the build plate may be formed via machining, blasting, laser ablation, chemical etching, etc.

At block 303, the method 300 may include forming a first layer atop the exterior surface of the build plate by depositing a plurality of powder structures over the plurality of peaks and within the plurality of indentations, at least a portion of the plurality of powder structures having an average width dimension that is greater than an average peak distance between adjacent peaks of the plurality of peaks. In some embodiments, the width dimension is a diameter.

At block 305, the method 300 may include thermally treating the plurality of powder structures, wherein the first layer covers the plurality of peaks following treatment. In some embodiments, the thermal treatment causes deformation of the tips of one or more of the plurality of peaks during the thermal treatment of the plurality of powder structures.

At block 307, the method 300 may optionally include forming a second layer over the first layer using, for example, an additive manufacturing technique, to form a finished medical device. In some embodiments, the second layer includes a second plurality of powdered structures deposited atop the first layer, and then thermally treated.

As used herein, an element or step recited in the singular and proceeded with the word "a" or "an" should be understood as not excluding plural elements or steps, unless such exclusion is explicitly recited. Furthermore, references to "one embodiment" of the present disclosure are not intended to be interpreted as excluding the existence of additional embodiments that also incorporate the recited features.

The use of "including," "comprising," or "having" and variations thereof herein is meant to encompass the items listed thereafter and equivalents thereof as well as additional items. Accordingly, the terms "including," "comprising," or "having" and variations thereof are open-ended expressions and can be used interchangeably herein.

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other.

Furthermore, identification references (e.g., primary, secondary, first, second, third, fourth, etc.) are not intended to connote importance or priority, but are used to distinguish one feature from another. The drawings are for purposes of illustration only and the dimensions, positions, order and relative sizes reflected in the drawings attached hereto may vary.

Furthermore, the terms "substantial" or "substantially," as well as the terms "approximate" or "approximately," can be used interchangeably in some embodiments, and can be described using any relative measures acceptable by one of ordinary skill in the art. For example, these terms can serve as a comparison to a reference parameter, to indicate a deviation capable of providing the intended function. Although non-limiting, the deviation from the reference parameter can be, for example, in an amount of less than 1%, less than 3%, less than 5%, less than 10%, less than 15%, less than 20%, and so on.

Still furthermore, although the illustrative methods are described above as a series of acts or events, the present disclosure is not limited by the illustrated ordering of such acts or events unless specifically stated. For example, some acts may occur in different orders and/or concurrently with other acts or events apart from those illustrated and/or described herein, in accordance with the disclosure. In addition, not all illustrated acts or events may be required to implement a methodology in accordance with the present disclosure. Furthermore, the methods may be implemented in association with the formation and/or processing of structures illustrated and described herein as well as in association with other structures not illustrated.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, the present disclosure has been described herein in the context of a particular implementation in a particular environment for a particular purpose. Those of ordinary skill in the art will recognize the usefulness is not limited thereto and the present disclosure may be beneficially implemented in any number of environments for any number of purposes.

What is claimed is:

1. A medical device, comprising:
   a build plate having a plurality of peaks and a plurality of indentations, the plurality of peaks and the plurality of indentations together defining a surface roughness of an exterior surface of the build plate; and
   a first layer formed atop the exterior surface of the build plate, the first layer comprising a plurality of powder structures disposed over the plurality of peaks and the plurality of indentations, wherein an average peak distance between adjacent peaks of the plurality of peaks is less than an average width dimension of at least a portion of the plurality of powder structures;
   wherein each peak of the plurality of peaks comprises a tip;
   wherein the plurality of powder structures are configured to melt to form a melt pool during a thermal treatment;
   wherein the tips of at least some of the plurality of peaks are configured to melt during the thermal treatment and mix together with the melt pool, solidifying to form the first layer as a consolidated first layer.

2. The medical device of claim 1, wherein the first layer covers the plurality of peaks.

3. The medical device of claim 1, further comprising a second layer formed over the first layer using an additive manufacturing technique.

4. The medical device of claim 3, wherein the second layer comprises a second plurality of powder structures.

5. The medical device of claim 4, wherein the average width dimension of the portion of the plurality of powder structures is different than a second average width dimension of the second plurality of powder structures.

6. The medical device of claim 4, wherein the plurality of powder structures and the second plurality of powder structures are spherically shaped.

7. The medical device of claim 1, wherein the build plate and the plurality of powder structures are different materials.

8. A method of forming a medical device, the method comprising:
   providing a build plate, the build plate having a plurality of peaks and a plurality of indentations, wherein the plurality of peaks and the plurality of indentations together define a surface roughness of an exterior surface of the build plate, and wherein each peak of the plurality of peaks comprises a tip; and
   forming a first layer atop the exterior surface of the build plate by:
      depositing a plurality of powder structures over the plurality of peaks and within the plurality of indentations, at least a portion of the plurality of powder structures having an average width dimension that is greater than an average peak distance between adjacent peaks of the plurality of peaks; and
      heating and melting the plurality of powder structures to form a melt pool;
      wherein the tips of at least some of the plurality of peaks melt during the heating of the plurality of powder structure and mix together with the melt pool, solidifying to form the first layer as a consolidated first layer; and
      wherein the first layer covers the plurality of peaks.

9. The method of claim 8, further comprising deforming a tip of one or more of the plurality of peaks during the heating of the plurality of powder structures.

10. The method of claim 8, further comprising forming a second layer over the first layer using an additive manufacturing technique.

11. The method of claim 8, wherein a thickness of the first layer is greater than a peak height of the plurality of peaks.

12. The method of claim 8, wherein depositing the plurality of powder structures comprises depositing a first group of the plurality of powder structures atop the exterior surface of the build plate, and depositing a second group of the plurality of powder structures atop the first group of the plurality of powder structures, wherein the first group of the plurality of powder structures has a first group average diameter and the second group of the plurality of powder structures has a second group average diameter, and wherein the first group average diameter is less than the second group average diameter.

13. A method of forming an implant, the method comprising:
   providing a build plate, the build plate having a plurality of alternating peaks and indentations, wherein the plurality of alternating peaks and indentations together define a surface roughness of an exterior surface of the build plate, and wherein each peak of the plurality of peaks comprises a tip; and
   forming a first layer atop the exterior surface of the build plate by:
      depositing a plurality of powder structures over the plurality of alternating peaks and indentations, at least a portion of the plurality of powder structures having an average width dimension that is greater than an average peak distance between adjacent peaks of the plurality of alternating peaks and indentations; and
      heating and melting the plurality of powder structures to form a melt pool;
   wherein the tips of at least some of the plurality of peaks melt during the heating of the plurality of powder structure and mix together with the melt pool, solidifying to form the first layer as a consolidated first layer; and
   wherein the first layer entirely covers the plurality of alternating peaks and indentations.

14. The method of claim 13, further comprising deforming a tip of one or more peaks of the plurality of alternating peaks and indentations during the heating of the plurality of powder structures.

15. The method of claim 13, further comprising forming, using an additive manufacturing technique, a second layer over a substantially planar upper surface of the first layer.

16. The method of claim 13, wherein a vertical thickness of the first layer is greater than a minimum peak height of the plurality of alternating peaks and indentations.

17. The method of claim 13, wherein depositing the plurality of powder structures comprises depositing a first group of the plurality of powder structures atop the exterior surface of the build plate, and depositing a second group of the plurality of powder structures atop the exterior surface of the build plate, wherein the first group of the plurality of powder structures has a first group average diameter and the second group of the plurality of powder structures has a second group average diameter, and wherein the first group average diameter is less than the second group average diameter.

18. The method of claim 17, wherein the first group of the plurality of powder structures is deposited before the second group of the plurality of powder structures is deposited.

19. The method of claim 17, wherein the first group of the plurality of powder structures and the second group of the plurality of powder are deposited simultaneously.

20. The method of claim 17, further comprising creating the build plate using an additive manufacturing technique.

\* \* \* \* \*